US008323295B2

(12) United States Patent
Hüfner et al.

(10) Patent No.: US 8,323,295 B2
(45) Date of Patent: Dec. 4, 2012

(54) MEDICAL CLAMP, IN PARTICULAR SPINAL CLAMP, DEVICE FOR PROVIDING A REFERENCE POSITION AND METHOD FOR DETERMINING A REFERENCE POSITION

(75) Inventors: Tobias Hüfner, Hannover (DE); Tim Dannenmann, Bamberg (DE); Musa Citak, Hannover (DE); Özcan Karsak, Herzogenaurach (DE)

(73) Assignee: Siemens AG, Munich (DE)

( * ) Notice: Subject to any disclaimer, the term of this patent is extended or adjusted under 35 U.S.C. 154(b) by 905 days.

(21) Appl. No.: 12/045,045

(22) Filed: Mar. 10, 2008

(65) Prior Publication Data

US 2008/0221625 A1    Sep. 11, 2008

(30) Foreign Application Priority Data

Mar. 8, 2007    (DE) .......................... 10 2007 011 568

(51) Int. Cl.
*A61B 17/58*    (2006.01)
*A61B 17/60*    (2006.01)
*A61F 2/00*    (2006.01)

(52) U.S. Cl. .......... 606/105; 606/246; 606/86 R; 606/90

(58) Field of Classification Search .................. 600/424, 600/218; 606/87, 102, 130, 151, 157, 205, 606/207, 208, 277, 324, 90, 105; 269/143, 269/249, 3, 6; 29/257, 276
See application file for complete search history.

(56) References Cited

U.S. PATENT DOCUMENTS

| | | | | |
|---|---|---|---|---|
| 2,429,356 A | * | 10/1947 | Hicks | 433/116 |
| 2,723,666 A | * | 11/1955 | Greenberg | 606/1 |
| 4,834,090 A | | 5/1989 | Moore | |
| 5,250,072 A | * | 10/1993 | Jain | 606/205 |
| 5,795,308 A | | 8/1998 | Russin | |
| 6,293,954 B1 | | 9/2001 | Fogarty et al. | |
| 6,726,472 B2 | * | 4/2004 | Kuhn | 33/514 |
| 6,926,712 B2 | * | 8/2005 | Phan | 606/41 |
| 7,422,591 B2 | * | 9/2008 | Phan | 606/51 |
| 7,497,029 B2 | * | 3/2009 | Plassky et al. | 33/645 |
| 2002/0038118 A1 | | 3/2002 | Shoham | |

(Continued)

FOREIGN PATENT DOCUMENTS

WO    0078233 A1    12/2000

(Continued)

OTHER PUBLICATIONS

European Search Report dated Jun. 5, 2008.

*Primary Examiner* — Andrew Yang
*Assistant Examiner* — Olivia C Chang
(74) *Attorney, Agent, or Firm* — Laurence A. Greenberg; Werner H. Stemer; Ralph E. Locher

(57) ABSTRACT

A medical clamp, in particular a spinal clamp, includes two clamp limbs connected to a grip part. The grip part executes a clamping movement of the clamp limbs and the clamp limbs are connected to the grip part in a releasable manner. The clamp permits particularly safe, minimally invasive percutaneous interventions, especially in the area of the spinal column. A device for using a medical clamp for providing a reference position for a positioning system for percutaneous interventions and a method for determining a reference position for a positioning system for percutaneous interventions, are also provided.

21 Claims, 3 Drawing Sheets

U.S. PATENT DOCUMENTS

| | | | |
|---|---|---|---|
| 2003/0225329 A1* | 12/2003 | Rossner et al. | 600/424 |
| 2004/0019263 A1* | 1/2004 | Jutras et al. | 600/407 |
| 2004/0039396 A1* | 2/2004 | Couture et al. | 606/87 |
| 2004/0102792 A1* | 5/2004 | Sarin et al. | 606/151 |
| 2006/0084867 A1 | 4/2006 | Tremblay et al. | |
| 2006/0142657 A1* | 6/2006 | Quaid et al. | 600/424 |
| 2006/0173377 A1* | 8/2006 | McCullough et al. | 600/566 |

FOREIGN PATENT DOCUMENTS

WO    03009768 A1    2/2003

* cited by examiner

MEDICAL CLAMP, IN PARTICULAR SPINAL CLAMP, DEVICE FOR PROVIDING A REFERENCE POSITION AND METHOD FOR DETERMINING A REFERENCE POSITION

CROSS-REFERENCE TO RELATED APPLICATION

This application claims the priority, under 35 U.S.C. §119, of German Patent Application DE 10 2007 011 568.9, filed Mar. 8, 2007; the prior application is herewith incorporated by reference in its entirety.

BACKGROUND OF THE INVENTION

Field of the Invention

The invention relates to a medical clamp, in particular a spinal clamp. The invention further relates to a device for using a medical clamp for providing a reference position for a positioning system for percutaneous interventions and to a method for determining a reference position for a positioning system for percutaneous interventions.

Image-assisted interventions, in particular CT-assisted interventions, are nowadays part of clinical routine. In contrast to invasive surgical treatment, minimally invasive image-assisted interventions allow the operator to work with minimal injury to the patient. That does not just reduce the clinical costs. It also reduces the danger of complications and has a positive cosmetic effect.

In order to carry out those image-assisted interventions, it is necessary to navigate medical instruments through the inside of the patient's body. The term navigation is understood as determining a position by a locating device, planning an access route to a target site and guiding a medical instrument to that target site along the planned access route. For that purpose, it is known to apply at least one reference marking (dynamic reference base (DRB)) to the patient's body.

For example, that can involve optical markings (for example spherical reflectors detectable by a camera) or electromagnetic markings (for example coils excited in an electromagnetic field). The position of the medical instrument relative to the patient's body can be determined with the aid of the reference marking and thus used for the navigation.

It has heretofore been customary for reference markings to be secured, for example affixed, to the patient's skin. In complex interventions, particularly in the area of the spinal column, that type of positioning of the reference markings is too imprecise for an exact navigation of the medical instrument. The reason therefor is that movements of the surface of the patient's body cannot be completely avoided. Reference markings therefore started to be secured directly to the patient's bone, for example by using nails or screws. In interventions on a patient's spinal column, the reference marking has heretofore been applied to exposed bones, for example to the spinous process, in most cases with the aid of clamps. All of those methods, however, require relatively invasive interventions in the patient, for which reason such a positioning of reference markings is complex and risky and, in addition, the above-mentioned advantages of a minimally invasive intervention are for the most part negated.

SUMMARY OF THE INVENTION

It is accordingly an object of the invention to provide a medical clamp, in particular a spinal clamp, a device for providing a reference position and a method for determining a reference position, which overcome the hereinafore-mentioned disadvantages of the heretofore-known devices and methods of this general type and which permit particularly safe, minimally invasive percutaneous interventions, especially in the area of the spinal column.

With the foregoing and other objects in view there is provided, in accordance with the invention, a medical clamp, in particular a spinal clamp, comprising two clamp limbs and a grip part connected to and releasable from the clamp limbs for executing a clamping movement of the clamp limbs.

The clamp is the embodiment of a number of fundamental concepts, all of which are based on the understanding that the use of the clamping method can be retained if a medical clamp can be made available which satisfies the requirements of a minimally invasive intervention and also takes into consideration the point of view of safe positioning of a reference marking.

According to a first underlying concept of the invention, the clamp has a modular construction in which the clamp limbs are connected to the grip part in a releasable manner. The fact that the clamp limbs can be released from the grip part means it is possible to use different clamp limbs, in particular those clamp limbs that are best suited for the individual case, i.e. the ones best suited to the specific anatomy. The modular construction of the clamp reduces the purchase costs, since the grip part only has to be purchased once. Instead of many different medical clamps, it is necessary to purchase just a single grip element and the necessary clamp limbs.

A further underlying concept of the invention is to use clamp limbs that are individually adapted to the particular anatomy of the site of use (e.g. the vertebral body). In particular, clamp limbs are used that have L-shaped or Y-shaped clamping jaws.

The Y-shaped clamping jaws are preferably used for particularly safe and rotationally stable fixation in the area of the lumbar spine. They are secured there to the spinous process. The Y-shape has the effect that the clamping force is distributed over a larger surface area, resulting in additional protection against twisting of the clamp.

The L-shaped clamping jaws are particularly suitable for the upper region of the thoracic spine, since there the spinous processes are narrower and extend horizontally.

A further underlying concept of the invention, when using straight clamping jaws, is to use a covering device which, during insertion of the clamp into the patient's body, covers the clamping jaws, which are often provided with points or edges. This avoids unnecessary damage to the tissue.

With the objects of the invention in view, there is also provided a device for providing a reference position for a positioning system for percutaneous interventions. The device comprises the medical clamp according to the invention.

With the objects of the invention in view, there is concomitantly provided a method for determining a reference position for a positioning system for percutaneous interventions. The method comprises providing the medical clamp according to the invention having a marking element, applying the medical clamp to a tissue part of a patient, and determining a position of the marking element with a contactless locating method.

Other features which are considered as characteristic for the invention are set forth in the appended claims.

Although the invention is illustrated and described herein as embodied in a medical clamp, in particular a spinal clamp, a device for providing a reference position and a method for determining a reference position, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL
VIEWS OF THE DRAWING

FIG. 1 is a diagrammatic, front-elevational view of a medical clamp with a reference marking for use in a positioning system for percutaneous interventions;

FIG. 2 includes first and second side-elevational views of a clamp limb with a straight clamping jaw, as depicted in FIG. 1;

FIG. 3 includes first and second side-elevational views of a covering device for a clamp limb, as depicted in FIG. 2;

FIG. 4 includes first and second side-elevational views of a clamp limb with a Y-shaped clamping jaw;

DETAILED DESCRIPTION OF THE INVENTION

The figures only show the invention diagrammatically and with its main component parts. All of the measurements are shown in millimeters. The indicated measurements are to be regarded as specific only to the example shown herein and serve only for purposes of illustration. All of the indicated measurements can be modified within the scope of the invention.

Figure 1:
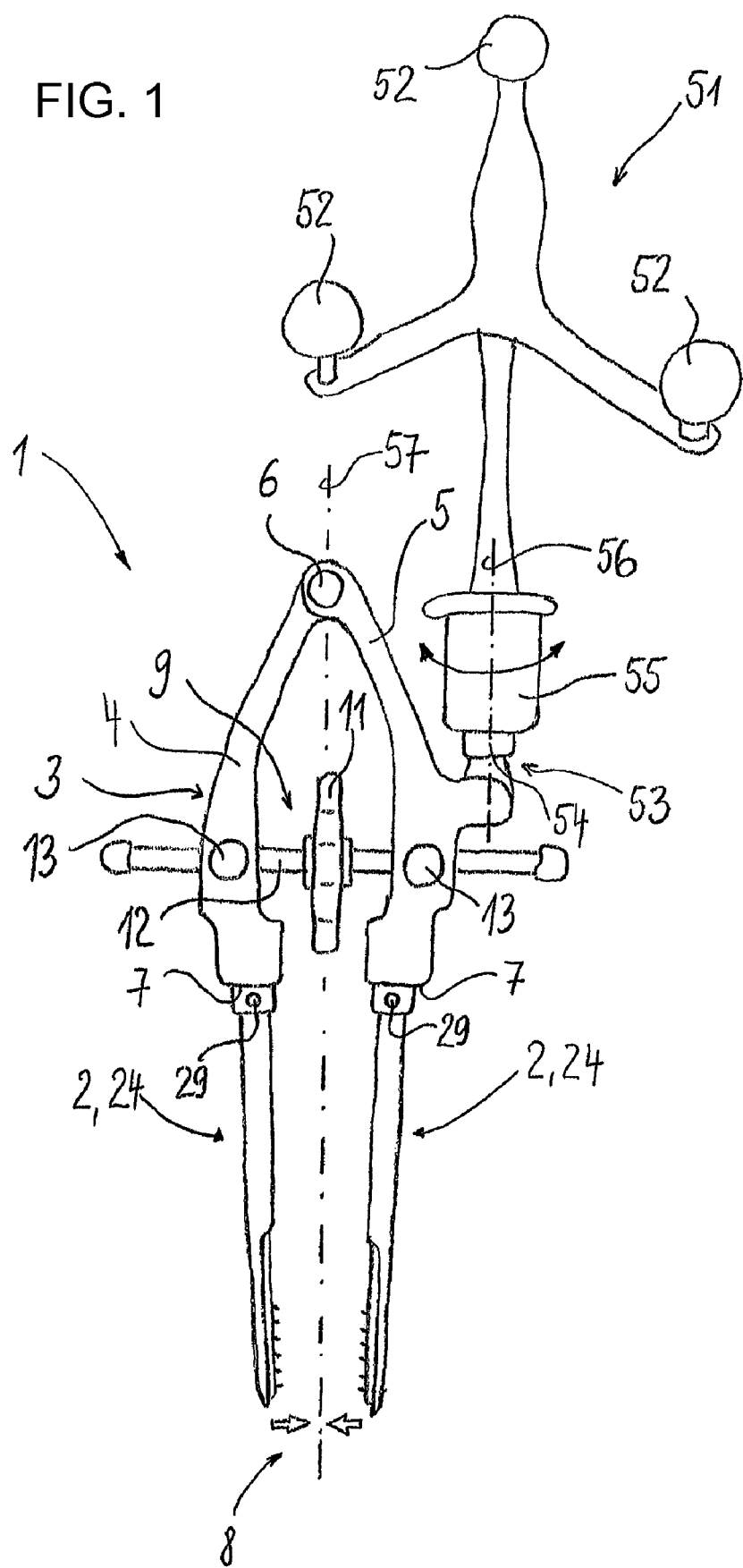

Referring now to the figures of the drawings in detail and first, particularly, to FIG. 1 thereof, there is seen a spinal clamp 1 according to the invention, which includes two clamp limbs 2 that are connected to a grip part 3, with the grip part 3 being constructed to execute a clamping movement of the clamp limbs 2. For this purpose, the grip part 3 has a first actuating limb 4 and a second actuating limb 5, which are movable relative to each other. The two actuating limbs 4, 5 are connected to each other at one of their ends through a pivot joint 6 in the manner of a compass. This stable and simple construction ensures a high degree of safety against failure.

End faces 7 of the grip part 3 that are directed away from the connection ends are spaced apart from each other when the clamp 1 is in an opened position, as shown in FIG. 1. This also results in a predetermined spacing of the clamp limbs 2, which allows the clamp limbs 2 to be inserted into the patient's body through two skin incisions spaced apart from each other. The skin incisions simply have to be dimensioned in such a way that they are able to receive the clamp limbs 2. Insertion of the grip part 3 into the body is not necessary.

In order to open and close a clamp mouth 8, the two actuating limbs 4, 5 can be moved towards and away from each other through a central drive mechanism 9. The central drive mechanism 9 includes a threaded spindle 12 provided with a knurled disc 11 and is preferably constructed to be self-locking. Thus, when securing the clamp 1 to a bone, it is possible to achieve a particularly firm and reliable fixation, with the clamp 1 being unable to automatically come loose. Elements 13 to be provided in the actuating limbs 4, 5 for the purpose of taking up the threaded spindle 12 will not be discussed in any detail herein, since technical constructions provided for this purpose are known to persons skilled in the art. As an alternative to a knurled disc, it is also possible to use a star-shaped wheel.

In FIG. 1, a position is shown in which the two clamp limbs 2 have already been moved slightly from a normal position, in which the two clamp limbs 2 are parallel to each other, and towards each other. The clamp limbs 2 are connected to the grip part 3 in an individually releasable manner. Thus, the clamp limbs 2 can also be individually replaced, for example in the case of a defect or the like, or if the anatomical situation so requires. The connection between the clamp limbs 2 and the grip part 3 is produced by snap-fitting, locking or clamping connections, for which non-illustrated corresponding receiving openings or connecting openings are provided in the lower end faces 7 of the actuating limbs. In this way, a simple but nevertheless very secure connection can be established. The drawings do not show securing elements that may be necessary on the clamp limbs 2. The measures necessary for suitably securing the clamp limbs 2 to the grip part 3 will not be discussed in any detail below.

Figure 2:
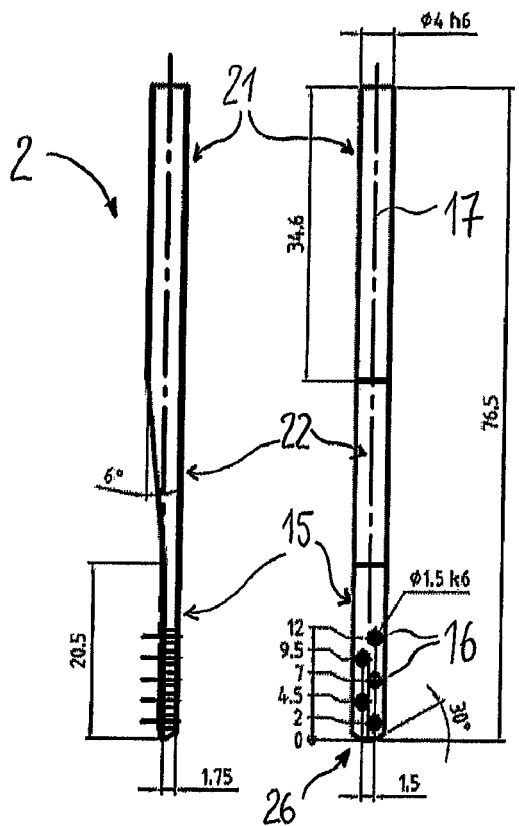

A clamp limb 2 of the kind shown in FIG. 1 has a straight clamping jaw 15, i.e. one that extends parallel to a central longitudinal axis 17 of the clamp limb 2, as seen in FIG. 2. The clamping jaw 15 has a length of 20.5 mm and is provided with fixing spikes 16 which are each offset by 1.5 mm relative to the central longitudinal axis or line 17 of the 76.5 mm long clamp limb, in order to achieve a better fixation to the bone tissue. The exact positioning of the fixing spikes 16 will be seen from the spacing dimensions indicated in FIG. 2.

Figure 7:
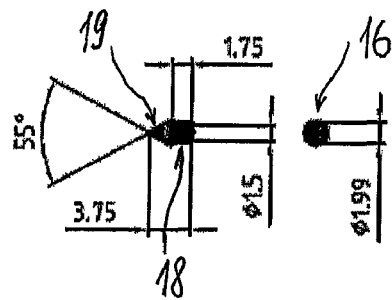
FIG. 7 includes a side-elevational view and a plan view of a clamp spike.

An example of a fixing spike 16 of this kind is shown in FIG. 7. A fixing spike 16 is preferably composed of a cylindrical shaft 18 and of a conical point 19 attached to the shaft 18. The point 19, at the site of attachment to the shaft 18, has a greater diameter (in this case 1.99 mm) than the shaft (in this case 1.5 mm) and therefore forms a kind of barb. In the example shown, the total length of the fixing spike 16 is 3.75 mm, with a shaft length of 1.75 mm. As the clamp 1 is closed, the fixing spikes 16 bore into the bone being operated on and avoid slipping of the clamp 1.

The thickness of the clamp limb 2 in the area of the clamping jaw 15 is less than the thickness of its attachment area 21. A bridge between the two skin incisions is preserved during use of the clamp 1 due to this tapering. The thickness of the clamp limb 2 decreases continuously in the direction of the clamping jaw 15 in a transition area 22. In the area of the clamping jaw 15, the thickness of the clamp limb 2 is only 1.75 mm. This prevents unnecessary damage to the tissue when introducing the clamp limbs 2 into the patient's body. The transition area 22 connects the proximal attachment area 21 of the clamp limb 2, which attachment area 21 has a length of 34.6 mm, to the distally disposed clamping jaw 15.

Figure 3:
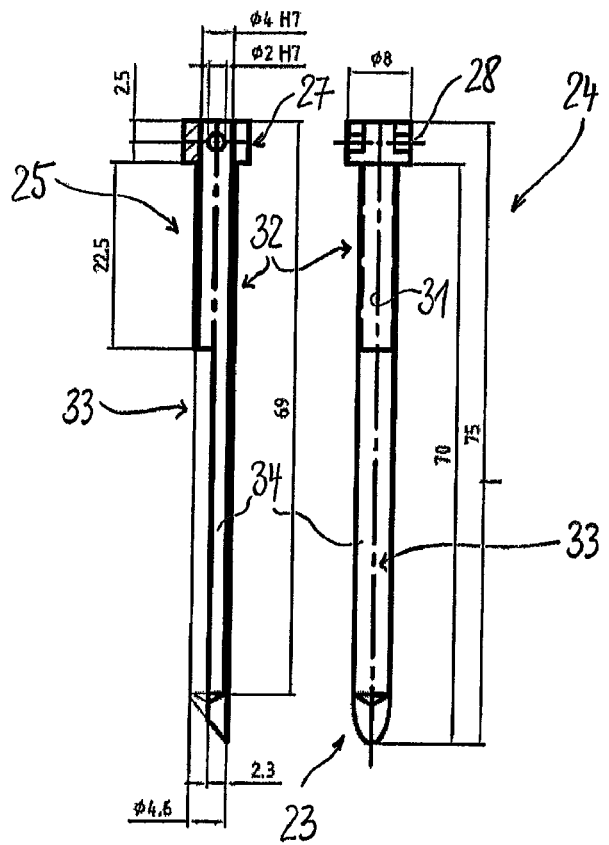

In order to ensure a minimally invasive application of the clamp 1, it is particularly advantageous to use a covering device 24, as shown in FIG. 3, to protect the tissue during insertion of the clamp limbs 2 into the patient's body. The covering device 24, which has an overall length of 75 mm, is constructed as a cylindrical sleeve 25 which is partially open to one side and which is pushed over the clamp limb 2 starting from a distal free end 26 of the clamp limb 2. Each clamp limb 2 is assigned a covering device 24.

The covering device 24 has an annular abutment 27 at the proximal end. The abutments 27 firstly serve to ensure that the covering devices 24, with respect to their displaceability in the longitudinal direction, assume an exactly defined position relative to the clamp limbs 2. As the clamp 1 is closed on the bone, the abutments 27 also serve to indicate the exact (preferably identical) position of the two sleeves 25 on the end faces 7 of the grip piece 3.

The abutment 27 is provided with lateral openings 28 for receiving an actuating pin 29. The pin 29, which is disposed perpendicular to a central longitudinal axis 31 of the sleeve 25 in the assembled state, serves as an actuating element for turning the sleeve 25 about its central longitudinal axis 31. In the open position of the sleeve 25 shown in FIG. 1, the pins 29 protrude from the plane of the drawing in the direction of the observer. The abutment 27, which is 5 mm wide, is adjoined at its bottom by a first closed sleeve part 32 measuring 22.5 mm in length. Thereafter, the sleeve 25 is opened by omission of one half of the sleeve. This opening 33 of the sleeve 25 results in a trough-shaped shield 34 formed by the remaining half of the sleeve and measuring 47.5 mm in length. This shield 34 also forms a distal end 23 of the sleeve and has a semicircular shape at that end in order to avoid unnecessary tissue damage during insertion of the clamp limb 2.

The dimensions of the clamp limb 2 and the covering device 24 are adapted to one another in such a way that the sleeve 25 can turn without difficulty around the clamp limb 2 in the assembled state.

The two covering devices 24 provided on a clamp 1 can also be actuated independently of each other, i.e. they can be moved independently of each other from a first position, in which they preferably completely cover the clamping jaw 15 of a clamp limb 2, to a second position, in which they do not cover the clamping jaw 15 of the clamp limb 2.

The principle of the covering device is not limited to clamp limbs 2 with straight clamping jaws 15. Clamp limbs with differently shaped clamping jaws can also be protected in this way.

Figure 4:
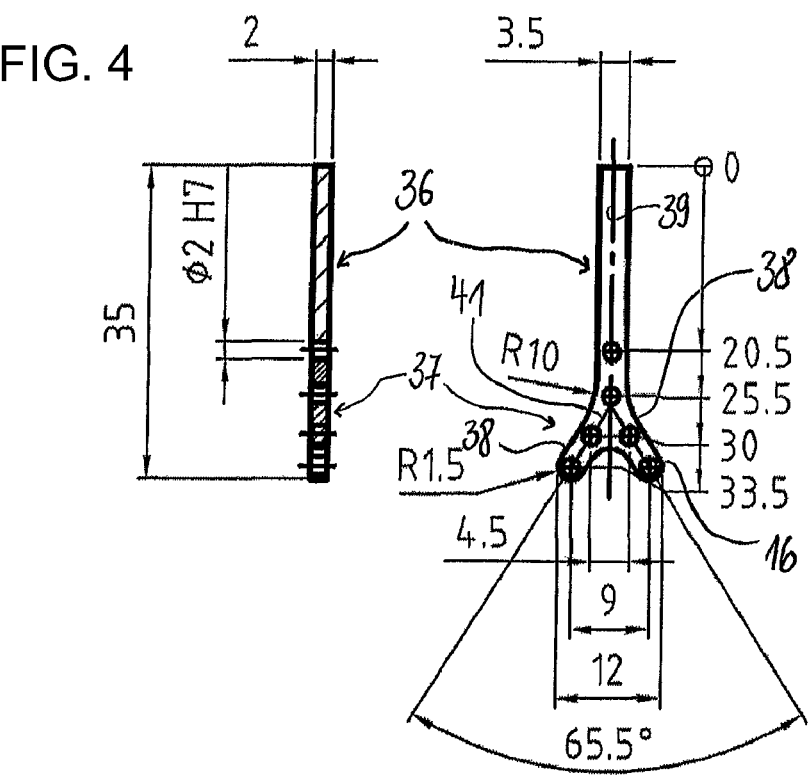

Instead of the clamp limbs 2 provided with a covering device 24, other clamp limbs can also be used with the grip part 3 shown in FIG. 1. For example, a clamp limb 36 measuring 35 mm in length and having a Y-shaped clamping jaw 37 is shown in FIG. 4. Clamping arms 38 of the Y-shaped clamping jaw 37 are angled symmetrically with respect to a central longitudinal axis 39 of the clamp limb 36 and have a maximum width of 12 mm at their distal end. The fixing spikes 16 provided there are then spaced apart from one another by 9 mm. The clamping arms 38 between them preferably enclose an angle of approximately 55° to 75°. An angle of approximately 60° to 70° has proven particularly advantageous for secure fixing. The clamp limb 36 shown in FIG. 4 has fixing spikes 16 disposed along a midline or midlines 41 of the clamping jaw 37 and the clamping arms 38. The exact dimensions of this clamp limb 36 and the positioning of the fixing spikes 16 will be seen from the measurements indicated in FIG. 4.

Figure 5:
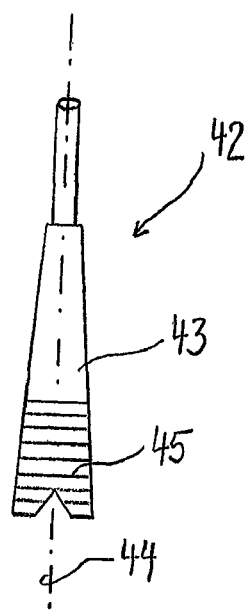
FIG. 5 is a side-elevational view of a clamp limb with another Y-shaped clamping jaw.

FIG. 5 shows another clamp limb 42 with a Y-shaped clamping jaw 43 which, in addition to a wider shape of the clamping jaw, is distinguished by the fact that, instead of the fixing spikes, it has been provided with fixing edges 45 or teeth that protrude obliquely outwards from the surface of the clamping jaw 43 and extend at right angles to a central longitudinal axis 44 of the clamp limb 42.

Figure 6:
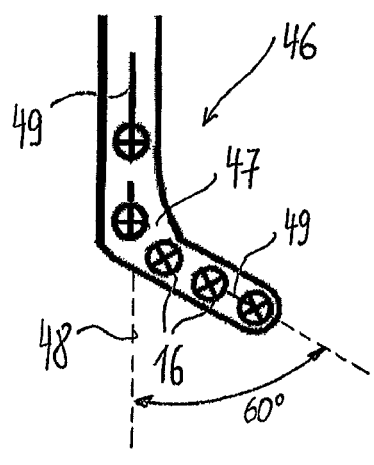
FIG. 6 is an enlarged, fragmentary, side-elevational view of a clamp limb with an L-shaped clamping jaw.

Alternatively, it is possible to use clamp limbs 46 with L-shaped clamping jaws 47, as is seen in FIG. 6. These preferably enclose an angle of approximately 20° to 90° with a central longitudinal axis 48 of the clamp limbs 46. An angle of approximately 40° to 70° has proven particularly advantageous for secure fixing. Fixing spikes 16 are provided in this case too and disposed along a midline 49 of the clamping jaw 47.

Both the grip part 3 and the clamp limbs 2 are preferably made of stainless and acid-resistant steel. However, if large parts of the clamp 1 are made of a radioparent material, the number of metal artifacts in an imaging method can be reduced. Preferred materials are polyether ether ketone, glass fiber, carbon-fiber-reinforced polyether ether ketone, carbon and ceramic. For example, the actuating limbs 4, 5 of the grip part 3 and the clamp limbs 2 can be made entirely of one of the above-mentioned non-metals. In addition, all of the elements of the clamp 1 are preferably made of a sterilizable material, in such a way that they can be reused after one application.

The clamp 1 according to the present invention has a reference marking 51 with reflectors 52 disposed in a star shape for use in an optical positioning system for percutaneous interventions. For example, the reflectors 52 are constructed in such a way that they are suitable for detection with an infrared camera. The reference marking 51 is connected to the grip part 3 of the clamp 1 by a securing device 53. The securing device 53 includes a coupling plug 54 onto which a coupling piece 55 of the reference marking 51 can be fitted. A longitudinal axis 56 of the coupling plug 54 is preferably placed as far as possible away from a central longitudinal axis 57 of the clamp 1, that is to say the axis of symmetry of the clamp. In the case of a reference marking 51 made of metal, this eccentric configuration reduces the metal artifacts in the imaging method, because the reference marking 51 is set away from the operating area.

The coupling piece 55 allows the reference marking 51 to rotate in such a way that the reflectors 52 are located in a position desired for navigation, which once again reduces the occurrence of metal artifacts.

The application of a medical clamp 1 according to the invention to a bone, for example to the spinous process of the spinal column, is described below. A clamp 1 with straight clamping jaws 15 and with a covering device 24 is used, by way of example. The patient is placed in the customary abdominal position. After sterile washing of surgical standard, the position of the required skin incisions is determined, for example with the aid of CT. The skin incisions are at most 1 to 1.5 cm long and are directly above the spinous process. After blunt cutting or exposure without cutting, the clamp limbs 2 of the spinal clamp 1 can be introduced through the skin incisions into the patient's body.

Before insertion, the covering device 24 is turned inwards in such a way that the clamping jaws 15 are covered and the fixing spikes 16 cannot lodge in the soft tissue and damage it. After checking the position of the clamp 1 through the use of the CT, the clamp 1 can be closed tight. The clamp mouth 8 is closed through the knurled disc 11, which is constructed in this case as a rotatable grip.

Once the modular clamp 1 has been secured to the patient's bone by a minimally invasive procedure, the position of the reference marking 51 fixed on the clamp 1 is determined with the aid of a contactless locating method and is used to navigate a surgical instrument or the like for surgery of the spinal column. Details concerning the structure and mode of functioning of the individual components of such a positioning system, in particular for collating and comparing data from the reference system on one hand and from the (CT) image data on the other hand, are known from the prior art and do not need to be dealt with any further herein.

After the navigation has been concluded, the clamping action is cancelled by simply turning the knurled disc 11 back. The wound can be closed according to surgical standard.

All of the features set forth in the description, in the attached claims and in the drawing may be important to the invention either individually or also in any desired combination with one another. In particular, the embodiments relating to the L-shaped clamping jaws 47 enclosing a particular angle with the central longitudinal axis 48 of the clamp limbs, the clamp limbs 36 having Y-shaped clamping jaws 37, and the clamping arms 38 of the Y-shaped clamping jaws 37 being angled preferably symmetrically with respect to the central longitudinal axis 39 of the clamp limbs 36 and between them enclosing a particular angle, can also be realized separately, i.e. independently of the embodiments described in the other claims, and in themselves each represent protectable inventions. At the same time, the embodiments relating to the covering device 24 being constructed as a tubular sleeve 25 which is at least partially open to one side, the covering device 24 being disposed on the clamp limb 2 in such a way that, in a first position of the covering device 24, the clamping jaw 15 of the clamp limb 2 is preferably completely covered by the covering device 24 and, in a second position of the covering device 24, the clamping jaw 15 of the clamp limb 2 is not covered by the covering device 24 and each clamp limb 2 being assigned a covering device 24, and the covering devices 24 being actuatable independently of each other, can also be realized separately, i.e. independently of the embodiments described in the other claims, and in itself also represents a protectable invention.

The invention claimed is:

1. A medical clamp, comprising:
   two clamp limbs each having a respective clamp jaw;
   a grip part connected to and releasable from said clamp limbs, said grip part being configured for executing a clamping movement of said clamp limbs;
   covering devices each being assigned to and disposed on a respective one of said clamp limbs, said covering devices being adapted for at least partially covering said clamp jaw of said respective clamp limb;
   each of said covering devices being a tubular sleeve, said tubular sleeves being at least partially open to one side and pushed over the respective one of said clamp limbs from a distal free end; and
   each of said covering devices being movable between a first position of said covering device in which said clamping jaw of said clamp limb is completely covered by said covering device and a second position of said covering device in which said clamping jaw of said clamp limb is not covered by said covering device;
   each of said tubular sleeves being movable between said first position and said second position by turning about its central longitudinal axis; and
   said tubular sleeves being actuatable independently of one another.

2. The medical clamp according to claim 1, wherein said grip part has a first actuating limb and a second actuating limb being movable relative to each other.

3. The medical clamp according to claim 2, wherein said two actuating limbs have ends and are connected to each other in an articulated manner at one of said ends.

4. The medical clamp according to claim 2, which further comprises a central drive mechanism for moving said two actuating limbs towards and away from each other.

5. The medical clamp according to claim 4, wherein said central drive mechanism includes a spindle with a knurled disc.

6. The medical clamp according to claim 1, wherein said clamp limbs are connected to said grip part by a connection selected from the group consisting of a snap-fitting connection, a locking connection and a clamping connection.

7. The medical clamp according to claim 1, wherein said clamp limbs are individually releasably connected to said grip part.

8. The medical clamp according to claim 1, wherein said clamp limbs have straight clamping jaws.

9. The medical clamp according to claim 8, wherein said clamp limbs each have an attachment end and a smaller thickness in vicinity of said clamping jaws than in vicinity of said attachment end.

10. The medical clamp according to claim 9, wherein said clamp limbs have a transition area and a thickness decreasing continuously in said transition area in direction of said clamping jaws.

11. The medical clamp according to claim 1, wherein said clamping jaw of said clamp limb is completely covered by said covering device in said first position of said covering device.

12. The medical clamp according to claim 1, wherein said covering device is one of two covering devices each being associated with a respective one of said clamp limbs and actuated independently of the other.

13. The medical clamp according to claim 1, wherein said clamp limbs have clamping jaws with fixing spikes or fixing edges.

14. The medical clamp according to claim 1, which further comprises parts made of a non-metal.

15. The medical clamp according to claim 1, wherein said grip part has a securing device for a marking element for determining a position of said grip part with a contactless locating method.

16. The medical clamp according to claim 15, wherein said marking element is a reference marking for a positioning system for percutaneous interventions.

17. The medical clamp according to claim 15, which further comprises a central longitudinal clamp axis, said marking element being disposed remote from said central longitudinal clamp axis.

18. The medical clamp according to claim 1, wherein the medical clamp is a spinal clamp.

19. In a positioning system for percutaneous interventions, a device for providing a reference position, the device comprising the medical clamp according to claim 1.

20. The medical clamp according to claim 1, wherein said covering devices are disposed on said clamp limbs in both said first and second positions of said covering devices.

21. A method for determining a reference position for a positioning system for percutaneous interventions, the method comprising the following steps:
   providing the medical clamp according to claim 1 having a marking element;
   applying the medical clamp to a tissue part of a patient; and
   determining a position of the marking element with a contactless locating method.

* * * * *